United States Patent [19]
Cramer et al.

[11] Patent Number: 6,102,937
[45] Date of Patent: Aug. 15, 2000

[54] DISPOSABLE THERMAL NECK WRAP

[75] Inventors: Ronald Dean Cramer, Cincinnati; Leane Kristine Davis, Milford; William Robert Ouellette, Cincinnati, all of Ohio

[73] Assignee: The Procter & Gamble Company, Cincinnati, Ohio

[21] Appl. No.: 08/777,642

[22] Filed: Dec. 31, 1996

[51] Int. Cl.[7] .................................................. A61F 7/00
[52] U.S. Cl. ........................ 607/109; 607/112; 607/114
[58] Field of Search .................... 607/96, 104, 108–112, 607/114; 165/46; 602/2; 126/204

[56] References Cited

U.S. PATENT DOCUMENTS

| | | | |
|---|---|---|---|
| Re. 32,026 | 11/1985 | Yamashita et al. | 126/263 |
| 1,491,539 | 4/1924 | Kirschmann . | |
| 2,547,886 | 4/1951 | Poux | 62/1 |
| 2,562,121 | 7/1951 | Poux | 150/2.2 |
| 2,602,302 | 7/1952 | Poux | 62/1 |
| 3,463,161 | 8/1969 | Andrassy | 128/402 |
| 3,900,035 | 8/1975 | Welch et al. | 128/402 |
| 4,034,747 | 7/1977 | Leroy | 128/68.1 |
| 4,095,583 | 6/1978 | Petersen et al. | 126/263 |
| 4,205,685 | 6/1980 | Yoshida et al. | 128/399 |
| 4,255,157 | 3/1981 | Yamaguchi et al. | 44/3 C |
| 4,268,272 | 5/1981 | Taura | 44/3 R |
| 4,282,005 | 8/1981 | Sato et al. | 44/3 R |
| 4,366,804 | 1/1983 | Abe | 126/263 |
| 4,462,224 | 7/1984 | Dunshee et al. | 607/114 X |
| 4,470,417 | 9/1984 | Gruber | 128/402 |
| 4,516,564 | 5/1985 | Koiso et al. | 126/263 |
| 4,575,097 | 3/1986 | Brannigan et al. | 128/402 |
| 4,649,895 | 3/1987 | Yasuki et al. | 126/263 |
| 4,753,241 | 6/1988 | Brannigan et al. | 128/380 |
| 4,756,299 | 7/1988 | Podella | 126/263 |
| 4,805,620 | 2/1989 | Meistrell | 128/402 |
| 4,860,748 | 8/1989 | Chiurco et al. | 128/399 |
| 4,886,063 | 12/1989 | Crews | 128/403 |
| 4,891,501 | 1/1990 | Lipton . | |
| 4,925,743 | 5/1990 | Ikeda et al. | 428/702 |
| 4,981,135 | 1/1991 | Hardy | 607/108 |
| 5,025,777 | 6/1991 | Hardwick | 126/263 |

(List continued on next page.)

FOREIGN PATENT DOCUMENTS

| | | |
|---|---|---|
| 0 014 300 A1 | 8/1980 | European Pat. Off. . |
| 0 370 600 A1 | 7/1989 | European Pat. Off. . |
| 160443 | 9/1983 | India . |
| 56-145846 | 11/1981 | Japan . |
| 57-170252 | 10/1982 | Japan . |
| 58-37075 | 3/1983 | Japan . |
| 3-100090 | 4/1991 | Japan . |
| 5-317188 | 12/1993 | Japan . |
| 6-1969 | 1/1994 | Japan . |
| 6-315498 | 11/1994 | Japan . |
| 6-343658 | 12/1994 | Japan . |
| 7-67907 | 3/1995 | Japan . |
| 7-124192 | 5/1995 | Japan . |
| 7-49042 | 5/1995 | Japan . |
| 7-194641 | 8/1995 | Japan . |
| 7-194642 | 8/1995 | Japan . |
| 8-98856 | 4/1996 | Japan . |
| 8-126656 | 5/1996 | Japan . |
| 2 205 496 | 12/1988 | United Kingdom . |
| WO 94/00087 | 1/1994 | WIPO . |

*Primary Examiner*—Jeffrey R. Jastrzab
*Assistant Examiner*—Ryan Carter
*Attorney, Agent, or Firm*—Loy M. White; Douglas C. Mohl; T. David Reed

[57] ABSTRACT

The present invention relates to disposable thermal neck wraps having one or more thermal packs comprising a unified structure having at least one continuous layer of semirigid material, which has different stiffness characteristics over a range of temperatures, and a plurality of heat cells, wherein the heat energy is applied to specific areas of the upper back, neck and shoulders. More particularly, the present invention relates to disposable thermal neck wraps having good conformity to user's upper back, neck, and shoulders which provides consistant, convienent, and comfortable heat application.

23 Claims, 2 Drawing Sheets

6,102,937
Page 2

U.S. PATENT DOCUMENTS

| | | | |
|---|---|---|---|
| 5,027,801 | 7/1991 | Grim | 128/80 H |
| 5,046,479 | 9/1991 | Usui | 126/204 |
| 5,072,598 | 12/1991 | Dibrell | 62/259.3 |
| 5,125,392 | 6/1992 | Hardwick | 126/263 |
| 5,148,804 | 9/1992 | Hill et al. | 128/402 |
| 5,211,949 | 5/1993 | Salyer | 607/108 X |
| 5,233,981 | 8/1993 | Miyashita . | |
| 5,247,928 | 9/1993 | Stilts, Jr. | 607/109 |
| 5,342,412 | 8/1994 | Ueki | 607/114 |
| 5,366,492 | 11/1994 | Ueki | 607/114 |
| 5,395,399 | 3/1995 | Rosenwald | 107/108 |
| 5,405,671 | 4/1995 | Kamin et al. | 428/69 |
| 5,496,357 | 3/1996 | Jensen et al. | 607/108 |
| 5,496,358 | 3/1996 | Rosenwald | 607/108 |
| 5,507,793 | 4/1996 | Hodges | 607/109 |
| 5,605,144 | 2/1997 | Simmons et al. | 126/204 |
| 5,674,270 | 10/1997 | Viltro et al. . | |

DISPOSABLE THERMAL NECK WRAP

TECHNICAL FIELD

The present invention relates to disposable thermal neck wraps having one or more thermal packs comprising a plurality of individual heat cells, wherein the heat energy is applied to specific areas of the upper back, neck and shoulders. More particularly, the present invention relates to disposable thermal neck wraps having good conformity to user's upper back, neck, and shoulders which provide consistant, convienent, and comfortable heat application.

BACKGROUND OF THE INVENTION

A common method of treating temporary or chronic pain is by application of heat to the afflicted area. Such heat treatments are used as a means of therapy for conditions which include aches, stiffness in muscles and joints, nerve pain, rheumatism and the like.

Upper back, neck, and shoulder pain is generally associated with stress, bursitis, and upper back and neck muscular problems. Heating pads, whirlpools, hot towels, and hydrocollators have been commonly used to relieve the pain caused by such problems. Many of these devices employ reusable thermal packs containing, e.g., water and/or microwaveable gels. In general, such devices which require the thermal source to be replenished are inconvenient to use. Further, many of these thermal units or devices do not provide long lasting heat and also do not maintain a consistent temperature over long periods of time. Depending on the length of exposure, the skin temperature needs to be maintained from about 35° C. to about 55° C., preferably from about 36° C. to about 45° C., more preferably from about 37° C. to about 43° C., and most preferably from about 38° C. to about 42° C., to achieve the desired therapeutic benefits.

The beneficial therapeutic effects from this administration of heat diminish after the heat source is removed. Therefore, depending on the temperature, it is desirable to provide a sustained heat source to the afflicted area for as long as possible, i.e., for about twenty minutes to about twelve hours, preferably for about four hours to about twelve hours, most preferably from about eight hours to about twelve hours. Disposable heat packs based on iron oxidation, such as those described in U.S. Pat. Nos. 4,366,804, 4,649,895, 5,046,479 and Re. Pat No. 32,026, are known. However, such devices have proven not totally satisfactory because many of these devices are bulky, cannot maintain a consistent and controlled temperature, have difficulty staying in place during use, and/or have unsatisfactory physical dimensions which hinder their effectiveness. Specifically, such devices cannot be easily incorporated into wraps which can comfortably conform to various body contours, and hence, they deliver short duration, inconsistent, inconvenient and/ or uncomfortable heat application to the body.

The present inventors have developed disposable thermal neck wraps comprising one or more thermal packs having a unified structure, wherein each thermal pack has at least one continuous layer of a semirigid material which is semirigid in specific areas of the thermal pack, yet which softens in between such areas when heated during use, preferably comprising a coextruded film of polypropylene and EVA. The thermal pack also comprises a plurality of individual heat cells, which typically comprise an exothermic composition, preferably comprising a specific iron oxidation chemistry and having specific physical dimensions and fill characteristics, spaced apart and fixedly attached across the thermal pack. Active heat cells, that is, heat cells having a temperature of from about 39° C. to about 60° C., preferably from about 40° C. to about 48° C., more preferably from about 41° C. to about 47° C., most preferably from about 42° C. to about 45° C., soften narrow portions of the continuous layer or layers of semirigid material which immediately surround the heat cells. All remaining portions of the continuous layer or layers which surround the softened portions remain more rigid. The narrow, softened portions act as hinges between each heat cell and the remaining, cooler, more rigid portions, bending preferentially more than either the heat cell or the more rigid portions. This results in thermal packs which possess sufficient rigidity to maintain structural support of the heat cells when oriented on an incline or vertically, to prevent unacceptable stretching of structures of the continuous layer or layers during processing or use, and to ensure child resistance, while still maintaining good overall drape characteristics when heated. The thermal pack, when incorporated into the neck wraps of the present invention, provide uniform heat coverage by having excellent conformity with the user's upper back, neck, and shoulders. These wraps also comprise alignment and position maintainance features.

It is therefore an object of the present invention to provide disposable thermal neck wraps which comprise one or more thermal packs, comprising a unified structure having at least one continuous layer of semirigid material, which has different stiffness characteristics over a range of temperatures, and a plurality of individual heat cells, which provide a controlled and sustained temperature and which reach their operating temperature range relatively quickly. The heat cells are spaced apart and fixedly attached across the unified structure of the thermal pack.

It is a further object of the present invention to provide thermal neck wraps which have good overall drapability while maintaining sufficient rigidity to maintain structural support of the heat cells when oriented on an incline or vertically, to prevent unacceptable stretching of the continuous layer or layers during processing or use, and/or to ensure child resistance.

It is a further object of the present invention to provide disposable thermal neck wraps which can be worn under outer clothing with minimal visibility, which have alignment and position maintenance features, and which have a thermal element pattern that directs thermal energy to where it has the most therapeutic benefit.

These objectives and additional objectives will become readily apparent from the detailed description which follows.

SUMMARY OF THE INVENTION

The disposable thermal neck wraps of the present invention comprise a substantially U-shaped piece of flexible material having a first arm portion, a second arm portion, a central body portion therebetween, a body-facing surface, and an opposing outer surface, such that when the neck wrap is placed on a user, the central body portion is centered at the user's upper back and lower neck. First and second arm portions lay over the user's shoulders toward the user's chest.

The disposable thermal neck wraps of the present invention further comprise one or more thermal packs. The thermal packs comprise a unified structure having at least one continuous layer of a coextruded material comprising a first side of polypropylene and a second side of a low melt temperature copolymer, which has different stiffness characteristics over a range of temperatures, and a plurality of individual heat cells spaced apart, which provide a controlled and sustained temperature and which reach their operating temperature range quickly. The heat cells are fixedly attached within each thermal pack. Each thermal pack provides good drapability while maintaining sufficient rigidity to maintain structural support of the heat cells, to prevent unacceptable stretching of the continuous layer or layers during prosessing or use, and ensure child resistance, while providing consistent, convenient and comfortable heat application. Preferably, the heat cells comprise a mixture of powdered iron, powdered carbon, water, and salt, which when exposed to oxygen, provides heat for several hours.

The disposable thermal neck wraps of the present invention further comprise one or more adhesive patches fixedly attached to one or both distal ends of first and second arm portions which serve to maintain the positioning of the thermal neck wrap during use by the wearer.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Figure 1:
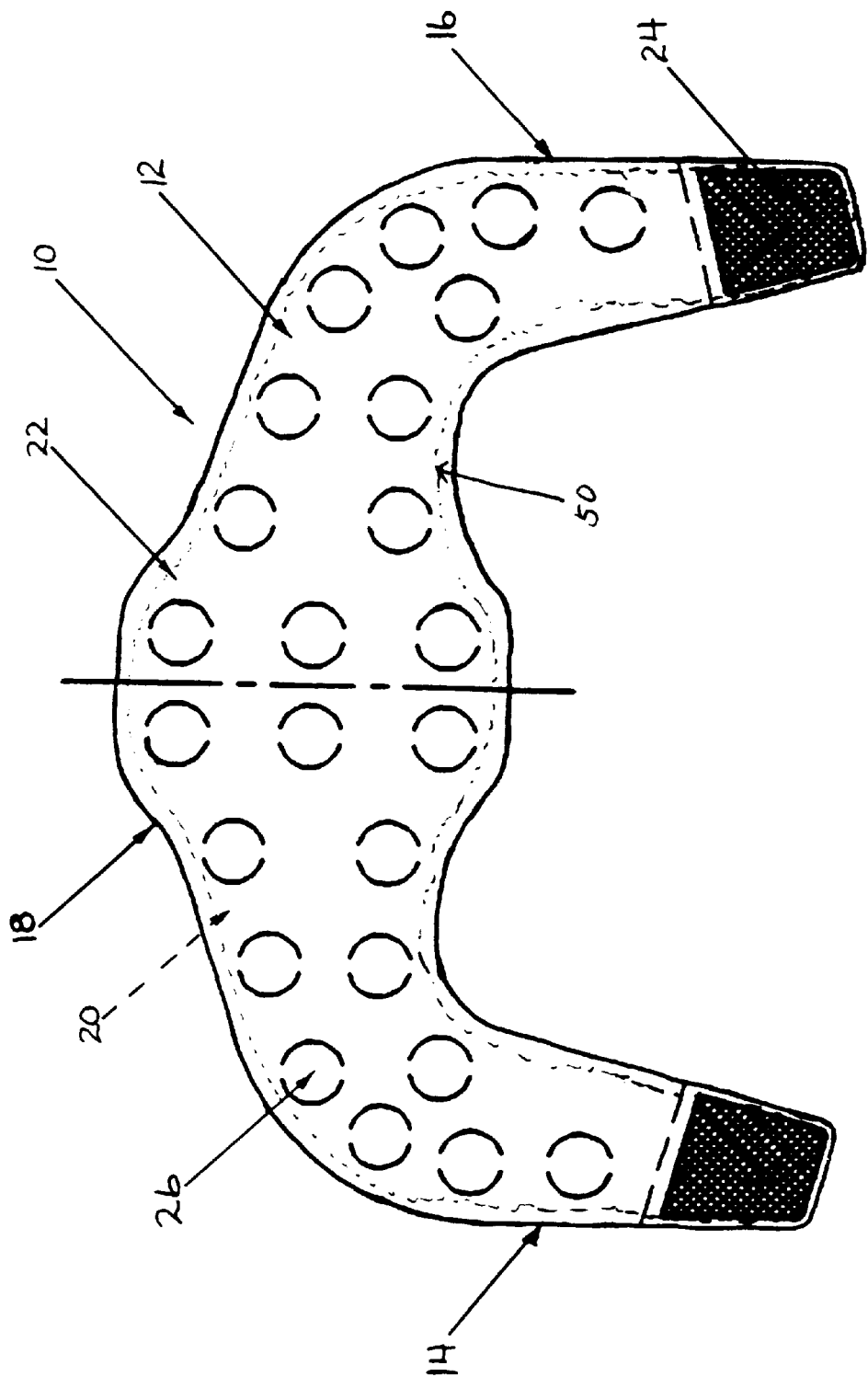
FIG. 1 is a top plan view of a preferred embodiment of the disposable thermal neck wrap of the present invention, showing a preferred pattern of thermal packs and/or heat cells.

The disposable thermal neck wraps of the present invention comprise one or more thermal packs having at least one continuous layer of a material, which exhibits specific thermophysical properties. The material is semirigid when at room temperature, i.e., about 25° C., or below, but softens and becomes substantially less rigid when heated to about 45° C. Therefore, when heat cells, which are fixedly attached to the structure of the thermal packs, are active, that is at a heat cell temperature of from about 39° C. to about 60° C., preferably from about 40° C. to about 48° C., more preferably from about 42° C. to about 47° C., and most preferably from about 44° C. to about 45° C., the narrow portion of the continuous layer or layers of material immediately surrounding each heat cell softens and acts as a hinge between the heat cell and the remaining, cooler, more rigid portion of the continuous layer or layers, bending preferentially more than either the heat cell or the more rigid portion. This results in thermal packs which possess sufficient rigidity to maintain structural support of the heat cells and prevent unacceptable stretching of structures of the continuous layer or layers during processing or use, while still maintaining good overall drape characteristics when heated. The disposable thermal neck wraps of the present invention provide consistent, convenient, and comfortable heat application, and an excellent conformity with user's upper back and the back portion of the user's neck, while retaining sufficient rigidity to ensure child resistance.

"Heat cells", as used herein, means a unified structure, comprising an exothermic composition, preferably a specific iron oxidation chemistry, enclosed within two layers, wherein at least one layer may be oxygen permeable, capable of providing long lasting heat generation with improved temperature control, and having specific physical dimensions and fill characteristics. These heat cells can be used as individual heating units, or in a thermal pack comprising a plurality of individual heat cells which can also be easily incorporated into disposable body wraps, pads, and the like. Thermal packs and body wraps incorporating thermal packs adapt to a wide variety of body contours, thus providing consistent, convenient, and comfortable heat application.

"Agglomerated pre-compaction composition", as used herein, means the mixture of dry powdered ingredients, comprising iron powder, carbonaceous powder, metal salt (s), water-holding agent(s), agglomeration aid(s), and dry binder(s) prior to direct compaction.

"Direct compaction", as used herein, means a dry powder mixture is blended, compressed, and formed into pellets, tablets, or slugs without the use of typical wet binders/ solutions to adhere the particulate(s) together. Alternatively, the dry powder mixture is blended and roll compacted or slugged, followed by milling and screening, creating directly compacted granules. Direct compaction may also be known as dry compaction.

"Heating element(s)", as used herein, means the exothermic, direct compacted, dry agglomerated pre-compaction composition formed into compaction articles, such as granules, pellets, slugs, and/or tablets capable of generating heat, after an aqueous solution such as water or brine (salt solution) is added, by the exothermic oxidation reaction of iron. Agglomeration granules of said agglomerated pre-compaction composition are also included as heating elements herein.

The "fill volume", as used herein, means the volume of the particulate composition or the compacted, water-swelled, heating element in the filled heat cell. The "void volume", as used herein, means the volume of the cell left unfilled by the particulate composition or the compacted, water-swelled, heating element in a finished heat cell, not including the unfilled space within a tablet comprising a hole or reservoir, in a finished heat cell, measured without differential pressure in the heat cell and without additional stretching or deformation of the substrate material. The "cell volume", as used herein, means the fill volume plus the void volume of the heat cell.

"Continuous layer or layers", as used herein, means one or more layers of a material which may be uninterrupted or partially, but not completely, interrupted by another material, holes, perforations, and the like, across its length and/or width.

"Semirigid material", as used herein, means a material which is rigid to some degree or in some parts and exhibits a toughness to maintain structural support of the heat cells in an unsupported format, and/or prevent unacceptable stretching of structures of the material during processing or use, while still maintaining good overall drape characteristics when heated, and/or retaining sufficient rigidity to ensure child resistance.

"Two dimensional drape", as used herein, means drape which occurs across a continuous layer or layers, across a thermal pack, or across a select region of a layer or layers, or thermal pack, exclusively along one axis, i.e., one fold line forms, at the expense of other axes in response to gravitational pull or other modest forces.

"Three dimensional drape", as used herein, means drape which simultaneously occurs across a continuous layer or layers, across a thermal pack, or across a select region of a layer or layers, or thermal pack, among two or more axes in response to gravitational pull or other modest forces.

It is understood that the disposable thermal neck wraps of the present invention may comprise one or more thermal packs. However, for clarity a disposable thermal neck wrap comprising a single thermal pack will be described herein.

Figure 2:
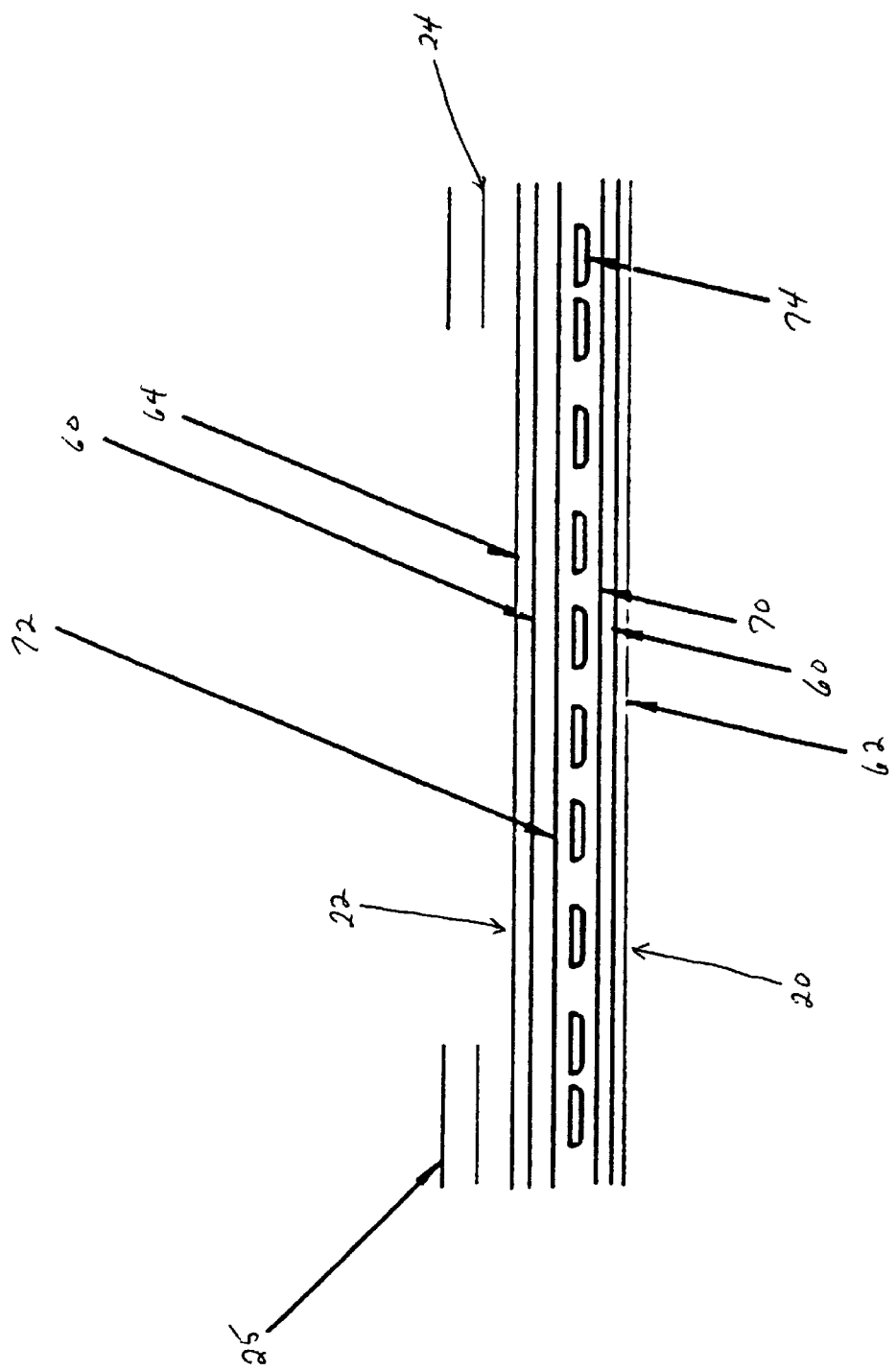
FIG. 2 is a sectioned elevation view of FIG. 1, showing the laminate structure of the thermal neck wrap.

Referring now to the drawings, and more particularly to FIGS. 1 and 2, there is shown a preferred embodiment of the present invention which provides a disposable thermal neck wrap with means for position maintenance, which is generally indicated as 10. Thermal neck wrap 10 comprises a piece of flexible material 12. Wrap 10 has a first arm portion 14, a second arm portion 16, and a central body portion 18 therebetween. Wrap 10 has a body-facing surface 20 and an opposing outer surface 22. When neck wrap 10 is worn, first and second arm portions 14 and 16 extend over the shoulders of the wearer toward the upper chest. Central body portion 18 is located on the user's upper back and the back portion of the user's neck.

Flexible material 12 of wrap 10 comprises body-facing material 62 and outer surface material 64. Body-facing material 62 and outer surface material 64 may be selected from any number of suitable materials including, but not limited to, wovens, knits, films, foams and nonwovens including spunbond, carded, meltblown, hydroentangled, through-air bonded, air laid, and wet laid. These materials may be made from natural fibers including, but not limited to, cotton, wool, linen, or manmade polymeric materials such as polypropylene, polyester, nylon, polyethylene, metallocene catalyst polyethylene, and the like.

A material that has been found to be particularly suitable for body-facing material 62 is a carded thermally bonded nonwoven of polypropylene with a basis weight of 54 grams per square yard (gsy). This material is available as grade #9354990 from Veratec, Walpole, Mass. A material that has been found to be particularly suitable for outer surface material 64 is a carded thermally bonded nonwoven of polypropylene with a basis weight of 27 gsy. This material is available as grade #9327786 from Veratec, Walpole, Mass.

Preferably, one or more adhesive patches 24 are fixedly attached to one or both of the distal ends of first and second arm portions 14 and 16. During use, thermal neck wrap 10 is draped over the shoulders of the wearer such that adhesive patches 24 are located toward the upper chest of the wearer and serve to maintain the positioning of thermal neck wrap 10. In a preferred embodiment of the present invention, adhesive patches 24 may be pressure sensitive adhesive circles, squares, or other shapes fixedly attached to body-facing surface 20 of first and second arms 14 and 16 near their respective distal ends, beyond the location of heat cells 26 of the thermal pack(s) 50, which are designed to reside in front of the shoulders, and of the heat cells 26 of thermal pack(s) 50 of body portion 18, which are designed to reside behind the shoulders of the wearer.

Adhesive patches 24 are protected prior to use by a removable release paper 25. Upon use, removable release paper 25 is removed exposing adhesive patches 24. Adhesive patches 24 may then be applied against the underside of the wearer's clothing, or adhesive patch 24 of first arm 14 may be applied to the body facing surface 20 of second arm 16, or adhesive patch 24 of second arm 16 may be applied to the body facing surface 20 of first arm 14.

Adhesive patches 24 may be any number of suitable adhesive materials which is capable of attaching to clothing. A particularly suitable material that has been used successfully is positioning adhesive 34-5598 available from National Starch and Chemical Co., Bridgewater, N.J. Release paper 25 may be any suitable polymeric film or paper which has been designed or treated to release from the adhesive used for adhesive patches 24. BL 25 MGA SILOX C3R/0 available from Akrosil has been shown to be suitable for this purpose.

Alternatively, adhesive patch 24 may be preapplied to a substrate prior to assembly of wrap 10. The substrate is then attached to outer surface material 64 by a suitable means.

The materials from which the wrap are constructed must be selected such that once they are combined in the product the product must be adapted to both easily drape over and conform to the body curvature and to provide minimal translation of compressive force along and in the plane of the product. In the present invention the layers are combined with pressure sensitive hot melt glue layers 60. Glue layer 60 is applied via a spiral glue application system at a level of approximately 0.002 to 0.010 grams per square inch. A particularly suitable adhesive for glue layer 60 is pressure sensitive hot melt adhesive 70-4589 available from National Starch & Chemical Co., Bridgewater, N.J. Alternatively, combining or assembly means may include, but not limited to, thermal dot bonding, melt blown hot melt glue, bead applied hot melt glue, ultrasonic, and/or pressure bonding.

It is necessary for the wrap to easily drape and conform to the body of the wearer to ensure intimate contact with the wearer during use. This intimate contact ensures that thermal energy is delivered properly and that frictional forces between the wearer and the wrap are maintained to minimize relative movement. The proper drape required is like that of a fabric as opposed to that of a paper. When a fabric is supported by a point force the fabric "breaks" or folds along multiple lines whereas a paper supported by the same point force will normally fold along a single line. Since the thermal neck wrap 10 of the present invention preferably conforms to the body in an area containing multiple compound curves, this "fabric-like" behavior is helpful.

It is also helpful for the thermal neck wrap 10 to provide minimal translation of any compressive forces within the plane(s) of the product. This means that if one side or edge of the wrap is subjected to a minimal compressive (or pushing) force that the wrap will buckle or fold locally and not transmit the force to other parts of the wrap. An example of this effect would be if a wearer of the wrap lifted one of the wearer's arms. In so doing the upper shoulder is rotated inward toward the neck, This inward movement of the shoulder produces a force on the edge of the wrap. Preferably, the thermal neck wrap 10 buckles or folds only on the side on which the compressive force is exerted, and therefore maintains its overall positioning relative to the user's body.

Thermal neck wrap 10 further comprises one or more thermal packs 50. Each thermal pack 50 is typically constructed by forming a pocket in a continuous base layer 70. The pocket in base layer 70 is then filled with an exothermic composition 74. After filling the pocket in base layer 70 with an exothermic composition 74, a cover layer 72 is placed over the pocket and heat sealed to base layer 70, encapsulating exothermic composition 74 forming heat cell 26.

Each thermal pack 50 comprises a plurality of individual heat cells 26, preferably embedded within the laminate structure of the thermal pack 50. These heat cells 26 are spaced apart from each other and each heat cell 26 functions independently of the rest of the heat cells 26. Each heat cell 26 contains a densely packed, particulate exothermic composition 74 which substantially fills the available cell volume within the cell reducing any excess void volume thereby minimizing the ability of the particulate matter to shift within the cell. Alternatively, the exothermic composition 74 may be compressed into a hard tablet before being placed in each cell. Because the heat generating material is densely packed or compressed into a tablet, the heat cells 26 are not readily flexible. Therefore, the spacing apart of the cells and the materials selected for base layer 70 and cover layer 72 between the heat cells 26 allows each thermal pack 50 to easily conform to the user's upper back, neck, and shoulders.

Alternatively, each thermal pack 50 may comprise a single continuous base layer 70, wherein individual heat cells 26 are fixedly attached and spaced apart across the base layer 70.

Heat cells 26 are positioned within thermal pack 50 such that they are located within central body portion 18 and first and second arms 14 and 16. When wrap 10 is properly positioned on the user, the heat cells 26 located away from first and second arms 14 and 16 are designed to reside behind or on top of the user's shoulders to approximate the shape and location of muscles in the user's upper back, lower neck, and shoulders. Heat cells 26 located near first and second arms 14 and 16 are designed to reside in front of or on top of the user's shoulders to provide a means of counter-balancing the weight of the heat cells 26 located in central body portion 18. Base layer 70 and cover layer 72 may be made of any number of thermoplastic materials which are semirigid at a temperature of about 25° C. and which soften, i.e., becomes substantially less rigid, at a temperature of about 45° C. Therefore, when heat cells 26, which are fixedly attached to the structure of the thermal pack 50, are active, that is at a heat cell temperature of from about 39° C. to about 60° C., preferably from about 40° C. to about 48° C., more preferably from about 41° C. to about 47° C., and most preferably from about 42° C. to about 45° C., the narrow portion of the continuous layer or layers of material immediately surrounding each heat cell softens and acts as a hinge between the heat cell and the remaining, cooler, more rigid portion of the continuous layer or layers, bending preferentially more than either the heat cell or the more rigid portion. This results in thermal pack 50 which possess sufficient rigidity to maintain structural support of the heat cells when oriented on an incline or vertically and to prevent unacceptable stretching of structures of the continuous layer or layers during processing or use, while still maintaining good overall drape characteristics when heated. When thermal pack 50 of the present invention is incorporated into neck wrap 10, neck wrap 10 easily adapts to a wide variety of body contours, provides consistent, convenient, and comfortable heat application, and an excellent conformity with body forms, while retaining sufficient rigidity to ensure child resistance.

Different materials may be capable of satisfying the specified requirement for the continuous layer or layers 70 and/or 72 provided that the thickness is adjusted accordingly. Such materials include, but are not limited to, polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof. These materials may be used alone or coextruded with a low melt temperature polymer including, but not limited to, ethylene vinyl acetate copolymer, low density polyethylene, and mixtures thereof. Such materials are also capable of containing exothermic composition 74 and limiting oxygen flow into heat cell 26, provides sufficient rigidity to prevent wrap 10 from folding or bunching during use, to prevent unacceptable stretching of structures of the continuous layer during processing or use, and to ensure child resistance.

Base layer 70 and cover layer 72 are preferably comprised of a coextruded film, having a first side of polypropylene and a second side of EVA, and having a combined thickness of from about 20 μm to about 30 μm, preferably about 25 μm. The two sides are coextruded such that they are thermally fused and can not be separated. The polypropylene comprises from about 10% to about 90%, preferably from about 40% to about 60%, of the thickness of base layer 70 and cover layer 72. When coextruded films of the type just described are used for base layer 70 and cover layer 70, the EVA sides are preferably orientied toward each other to facilitate thermal bonding of cover layer 70 to base layer 72. A particularly suitable material is available as P18-3161 from Clopay Plastics Products, Cincinnati, Ohio, or Terre Haute, Ind. The P18-3161 which is preferable for cell covering 72 has been subjected to a post process aperturing with hot needles to render it permeable to oxygen.

When coextruded films of the type just described are used for cell forming base layer 70 and cell covering layer 72, the EVA sides are preferably oriented toward each other to facilitate thermal bonding of cell covering layer 72 to cell forming base layer 70.

Exothermic composition 74 may comprise any composition capable of providing heat. However, exothermic composition 74 preferably comprises a particulate mix of chemical compounds that undergo an oxidation reaction during use. Exothermic composition 74 may also be formed into agglomerated granules, direct compacted into compaction articles such as granules, pellets, tablets, and/or slugs, and mixtures thereof. The mix of compounds typically comprises iron powder, carbon, a metal salt(s), and water. Mixtures of this type react when exposed to oxygen, providing heat for several hours.

Suitable sources for iron powder include cast iron powder, reduced iron powder, electrolytic iron powder, scrap iron powder, pig iron, wrought iron, various steels, iron alloys, and the like and treated varieties of these iron powders. There is no particular limitation to their purity, kind, etc. so long as it can be used to produce heat-generation with electrically conducting water and air. Typically, the iron powder comprises from about 30% to about 80% by weight, preferably from about 50% to about 70% by weight, of the particulate exothermic composition.

Active carbon prepared from coconut shell, wood, charcoal, coal, bone coal, etc. are useful, but those prepared from other raw materials such as animal products, natural gas, fats, oils and resins are also useful in the particulate exothermic composition of the present invention. There is no limitation to the kinds of active carbon used, however, the preferred active carbon has superior water holding capabilities and the different carbons may be blended to reduce cost. Therefore, mixtures of the above carbons are useful in the present invention as well. Typically, activated carbon, non-activated carbon, and mixtures thereof, comprises from about 3% to about 25%, preferably from about 8% to about 20%, most preferably from about 9% to about 15% by weight, of the particulate exothermic composition.

The metal salts useful in the particulate exothermic composition include sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Also, carbonate salts, acetate salts, nitrates, nitrites and other salts can be used. In general, several suitable alkali, alkaline earth, and transition metal salts exist which can also be used, alone or in combination, to sustain the corrosive reaction of iron. The preferred metal salts are sodium chloride, cupric chloride, and mixtures thereof. Typically, the metal salt(s) comprises from about 0.5% to about 10% by weight, preferably from about 1.0% to about 5% by weight, of the particulate exothermic composition.

The water used in the particulate exothermic composition may be from any appropriate source. There is no particular limitation to its purity, kind, etc. Typically, water comprises from about 1% to about 40% by weight, preferably from about 10% to about 30% by weight, of the particulate exothermic composition.

Additional water-holding materials may also be added as appropriate. Useful additional water-holding materials include vermiculite, porous silicates, wood powder, wood flour, cotton cloth having a large amount of fluffs, short fibers of cotton, paper scrap, vegetable matter, super absorbent water-swellable or water-soluble polymers and resins, carboxymethylcellulose salts, and other porous materials having a large capillary function and hydrophilic property can be used. Typically, the additional water-holding materials comprise from about 0.1% to about 30% by weight, preferably from about 0.5% to about 20% by weight, most preferably from about 1% to about 10% by weight, of the particulate exothermic composition.

Other additional components include agglomeration aids such as gelatin, natural gums, cellulose derivatives, cellulose ethers and their derivatives, starch, modified starches, polyvinyl alcohols, polyvinylpyrrolidone, sodium alginates, polyols, glycols, corn syrup, sucrose syrup, sorbitol syrup and other polysaccharides and their derivatives, polyacrylamides, polyvinyloxoazolidone, and maltitol syrup; dry binders such as maltodextrin, sprayed lactose, co-crystallized sucrose and dextrin, modified dextrose, sorbitol, mannitol, microcrystalline cellulose, microfine cellulose, pre-gelatinized starch, dicalcium phosphate, and calcium carbonate; oxidation reaction enhancers such as elemental chromium, manganese, or copper, compounds comprising said elements, or mixtures thereof; hydrogen gas inhibitors such as inorganic or organic alkali compounds or alkali weak acid salts including sodium hydroxide, potassium hydroxide, sodium hydrogen carbonate, sodium carbonate, calcium hydroxide, calcium carbonate, and sodium propionate; fillers such as natural cellulosic fragments including wood dust, cotton linter, and cellulose, synthetic fibers in fragmentary form including polyester fibers, foamed synthetic resins such as foamed polystyrene and polyurethane, and inorganic compounds including silica powder, porous silica gel, sodium sulfate, barium sulfate, iron oxides, and alumina; and anti-caking agents such as tricalcium phosphate and sodium silicoaluminate. Such components also include thickeners such as cornstarch, potato starch, carboxymethylcellulose, and $\alpha$-starch, and surfactants such as those included within the anionic, cationic, nonionic, zwitterionic, and amphoteric types. The preferred surfactant, if used however, is nonionic. Still other additional components which may be added to the particulate exothermic compositions of the present invention, as appropriate, include extending agents such as metasilicates, zirconium, and ceramics.

The heat cells 26 of each thermal pack 50 can have any geometric shape, e.g., disk, triangle, pyramid, cone, sphere, square, cube, rectangle, rectangular parallelepiped, cylinder, ellipsoid and the like. The preferred shape of the heat cells 26 comprises a disk shaped geometry having a cell diameter of from about 0.2 cm to about 10 cm, preferably from about 0.5 cm to about 8 cm, more preferably from about 1 cm to about 5 cm, and most preferably from about 1.5 cm to about 3 cm. The heat cells 26 have a height of from about 0.08 cm to about 1 cm, preferably from about 0.15 cm to about 0.9 cm, more preferably greater than from about 0.2 cm to about 0.8 cm, and most preferably about 0.4 cm.

The ratio of fill volume to cell volume of the heat cells 26 is from about 0.7 to about 1.0, preferably from about 0.75 to about 1.0, more preferably from about 0.8 to about 1.0, even more preferably from about 0.85 to about 1.0, and most preferably from about 0.9 to about 1.0.

Oxygen permeability can be provided by selecting materials for the base layer 70 and/or cover layer 72 that have the specifically desired permeability properties. The desired permeability properties may be provided by microporous films or by films which have pores or holes formed therein. The formation of these holes/pores may be via extrusion cast/vacuum formation or by hot needle aperturing. The size of the apertures is preferably about 0.127 mm diameter, and there are preferably 25 to 40 apertures per heat cell 26. Another preferred method of making apertures is to pierce cell covering layer 72 with cold needles. Alternatively, apertures may be produced by a vacuum forming or a high pressure water jet forming process. Oxygen permeability may also be provided in the present invention by perforating at least one of the base layer 70 and cover layer 72 with aeration holes using, for example, an array of pins having tapered points and diameters of from about 0.2 mm to about 2 mm, preferably from about 0.4 mm to about 0.9 mm. The array of pins is patterned such that the base layer 70 and/or cover layer 72 are perforated by from about 10 to about 30 pins per square centimeter. Alternatively, after the base layer 70 and cover layer 72 have been bonded together, enclosing the exothermic composition 74 in the pocket between them, one side of the heat cells 26 may be perforated with aeration holes using, for example, at least one pin, preferably an array of from about 20 to about 60 pins having tapered points and diameters of from about 0.2 mm to about 2 mm, preferably from about 0.4 mm to about 0.9 mm. The pins are pressed through one side of the base layer 70 and/or cover layer 72 to a depth of from about 2% to about 100%, preferably from about 20% to about 100%, and more preferably from about 50% to about 100% into the exothermic composition 74. This hole configuration provides an oxygen diffusion into the heat cell 26 during oxidation of the particulate exothermic composition 74 of from about 0.01 cc $O_2$/min./5 cm$^2$ to about 15.0 cc $O_2$/min./5 cm$^2$ (at 21° C., 1 ATM), preferably from about 0.9 cc $O_2$/min./5 cm$^2$ to about 3 cc $O_2$/min./5 cm$^2$ (at 21° C., 1 ATM).

The velocity, duration, and temperature of the thermogenic oxidation reaction of the exothermic composition 74 can be controlled as desired by changing the area of contact with air, more specifically, by changing the oxygen diffusion/permeability.

Thermal neck wrap 10 has overall dimensions of about 300 mm by about 425 mm.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A disposable thermal neck wrap comprising:
   A) at least one substantially U-shape piece of flexible material, said piece of flexible material having a first arm portion, a second arm portion, and a central body portion therebetween, such that when said neck wrap is placed on a user, said central body portion is centered at said user's upper back and lower neck and said first and second arm portions lay across said user's shoulders toward said user's chest; and
   B) one or more thermal packs fixedly attached within or to said at least one piece of flexible material, wherein said thermal pack has a unified structure comprising:
      a) at least one continuous layer comprising a single sheet or film having a first side of polypropylene and a second side of a low melt temperature copolymer, wherein said continuous layer is coextruded such that said first side and said second side are thermally fused and can not be separated, and wherein sad continuous layer is semirigid at a temperature of about 25° C. and substantially less rigid at a temperature of about 45° C.; and
      b) a plurality of individual heat cells spaced apart and fixed within or to said unified structure of said thermal pack.

2. A disposable thermal neck wrap according to claim 1 wherein said continuous layer comprises a coextruded film having a first side of polypropylene and a second side of ethylene vinyl acetate copolymer, wherein said polypropylene comprises from about 10% to about 90% of the total thickness of said film.

3. A disposable thermal neck wrap according to claim 2 wherein said continuous layer comprises a coextruded film having a first side of polypropylene and a second side of ethylene vinyl acetate copolymer, wherein said polypropylene comprises from about 40% to about 60% of the total thickness of said film.

4. A disposable thermal neck wrap according to claim 3 wherein said continuous layer has a thickness of from about 20 μm to about 30 μm.

5. A disposable thermal neck wrap according to claim 1 further comprising one or more adhesive patches attached to distal ends of at least one of said first and second arm portions.

6. A disposable thermal neck wrap according to claim 5 wherein said adhesive patches comprise pressure sensitive adhesive patches selected from the group consisting of circles, squares, other shapes, and mixtures thereof.

7. A disposable thermal neck wrap according to claim 1 wherein one or more of said heat cells of said thermal packs are located within each of said arms.

8. A disposable thermal neck wrap according to claim 1 wherein said heat cells comprise an exothermic composition which comprises:
   a.) from about 30% to about 80% iron powder;
   b.) from about 3% to about 25% activated carbon, non-activated carbon, and mixtures thereof;
   c.) from about 0.5% to about 10% metal salt; and
   d.) from about 1% to about 40% water.

9. A disposable thermal neck wrap according to claim 8 wherein said heat cells comprise from about 0.1% to about 30% of additional water-holding material.

10. A disposable thermal neck wrap according to claim 8 wherein said heat cells comprise the shape of a disk having a diameter of from about 0.2 cm to about 10 cm and a height of from about 0.08 cm to about 1 cm.

11. A disposable thermal neck wrap according to claim 1 wherein said heat cells comprise an exothermic composition which comprises:
   a.) from about 30% to about 80% of iron powder;
   b.) from about 3% to about 20% of carbonaceous material selected from the group consisting of activated carbon, non-activated carbon, and mixtures thereof;
   c.) from about 0% to about 9% of an agglomeration aid selected from the group consisting of corn syrup, maltitol syrup, crystallizing sorbitol syrup, amorphous sorbitol syrup, and mixtures thereof; and
   d.) from about 0% to about 35% of a dry binder selected from the group consisting of microcrystalline cellulose, maltodextrin, sprayed lactose, co-crystallized sucrose and dextrin, modified dextrose, mannitol, microfine cellulose, pre-gelatinized starch, dicalcium phosphate, calcium carbonate, and mixtures thereof;
   wherein from about 0.5% to about 10% of a metal salt selected from the group consisting of alkali metal salts, alkaline earth metal salts, transitional metal salts, and mixtures thereof is added to said composition as part of the dry mix or subsequently in an aqueous solution as brine, and further wherein said exothermic composition comprises a physical form selected from the group consisting of dry agglomerated granules, direct compaction articles, and mixtures thereof.

12. A disposable thermal neck wrap according to claim 11 wherein said heat cells further comprise from about 0.5% to about 10% of additional water-holding materials selected from the group consisting of acrylic acid salt starch co-polymer, isobutylene maleic anhydride co-polymer, vermiculite, carboxymethylcellulose, and mixtures thereof.

13. A disposable thermal neck wrap according to claim 11 wherein said dry binder comprises from about 4% to about 30% of microcrystalline cellulose.

14. A disposable thermal neck wrap according to claim 11 wherein said metal salt comprises sodium chloride.

15. A disposable thermal neck wrap according to claim 11 wherein said heat cells are activated by the addition of an aqueous solution.

16. A disposable thermal neck wrap according to claim 11 wherein said direct compaction articles are selected from the group consisting of granules, pellets, tablets, slugs, and mixtures thereof wherein said tablets and slugs comprise a geometric shape selected from the group consisting of disk, triangle, square, cube, rectangle, cylinder, and ellipsoid.

17. A disposable thermal neck wrap according to claim 16 wherein said tablets and slugs comprise a disk shaped geometry having a diameter of from about 0.2 cm to about 10 cm and a height of from about 0.08 cm to about 1.0 cm.

18. A disposable thermal neck wrap according to claim 17 wherein said tablets comprise a geometric shape selected from the group consisting of a disk shape wherein a hole passes perpendicular to and through the middle of the top and bottom surfaces and a disk shape wherein the top and bottom surfaces are concaved forming a reservoir conducive to holding a liquid.

19. A disposable thermal neck wrap according to claim 18 wherein said tablets comprise a disk shape wherein a hole passes perpendicular to and through the middle of the top and bottom surfaces.

20. A disposable thermal neck wrap according to claim 16 wherein said direct compaction articles comprise a density of greater than about 1 g/cm$^3$.

21. A disposable thermal neck wrap according to claim 20 wherein said direct compaction articles comprise a density of from about 1.5 g/cm$^3$ to about 3.0 g/cm$^3$.

22. A method of treating upper back, neck, and shoulder pain by applying a disposable thermal neck wrap of claim 1 to the upper back, neck, and shoulders of a person needing such treatment.

23. A disposable thermal neck wrap according to claim 1 wherein said thermal pack comprises a unified structure having at least two said continuous layers, wherein said second sides of said at least two continuous layers are oriented toward each other to facilitate thermal bonding of said at least two continuous layers.

* * * * *